United States Patent [19]

Dagani

[11] 4,388,468

[45] Jun. 14, 1983

[54] PROCESS FOR PRODUCING SUBSTITUTED PYRROLES

[75] Inventor: Michael J. Dagani, Baton Rouge, La.

[73] Assignee: Ethyl Corporation, Richmond, Va.

[21] Appl. No.: 293,853

[22] Filed: Aug. 18, 1981

Related U.S. Application Data

[63] Continuation-in-part of Ser. No. 137,511, Apr. 4, 1980, abandoned.

[51] Int. Cl.$^3$ ............................................ C07D 207/34
[52] U.S. Cl. .................................... 548/531; 548/536
[58] Field of Search ...................... 260/326.47, 326.46; 548/531

[56] References Cited

U.S. PATENT DOCUMENTS 3,952,012 4/1976 Carson ............................ 260/326.47
4,048,191 9/1977 Carson ............................ 260/326.47

OTHER PUBLICATIONS

Elderfield, Heterocyclic Compounds, vol. 1, (New York, 1950), pp. 132–134.

Primary Examiner—Alton D. Rollins
Attorney, Agent, or Firm—Donald L. Johnson; John F. Sieberth; Willard G. Montgomery

[57] ABSTRACT

A process for the preparation of certain 4-alkyl substituted 5-aroyl-pyrrole alkanoic acids useful as intermediates for anti-inflammatory agents.

11 Claims, No Drawings

PROCESS FOR PRODUCING SUBSTITUTED PYRROLES

CROSS REFERENCE TO RELATED APPLICATION

This application is a continuation-in-part of pending application Ser. No. 137,511 filed: Apr. 4, 1980, abandoned.

BACKGROUND OF THE INVENTION

This invention relates to a process for producing substituted pyrroles, especially pyrrole-2-acetic acids and derivative compounds thereof. More particularly, the process of this invention is concerned with processes which produce 1,4-diloweralkyl-3-lower-alkoxycarbonyl-pyrrole-2-acetate which is a useful intermediate for analgesic and anti-inflammatory pharmaceutical compounds.

It has been found difficult in the past to substitute pyrrole rings, which already contain substituents at other positions on the rings, at the 4-position because of steric hindrance and ring deactivation. Thus, Carson, U.S. Pat. Nos. 3,752,826 and 3,865,840, teach the preparation of certain 4-substituted 5-aroyl-pyrrole alkanoic acids and the corresponding salts, esters, nitriles, amides, and substituted amides thereof represented by the formulas:

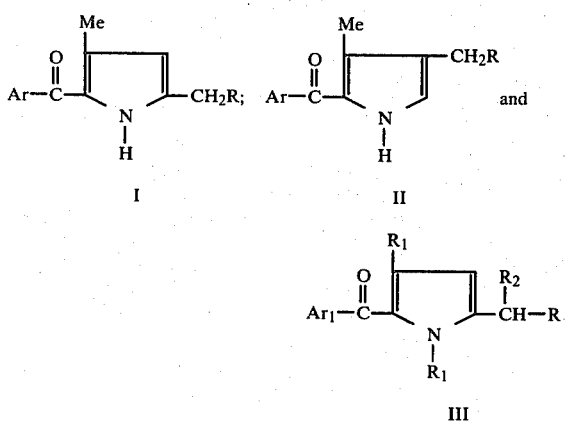

wherein:
Ar represents a member selected from the group consisting of phenyl, monosubstituted phenyl and polysubstituted phenyl, each substituent of said substituted phenyls being a member selected from the group consisting of halo, lower alkyl and lower alkoxy;
$Ar_1$ represents a member selected from the group consisting of phenyl, thienyl, 5-methylthienyl, monosubstituted phenyl and polysubstituted phenyl, each substituent of said substituted phenyls being a member selected from the group consisting of halo, lower alkyl, trifluoromethyl, lower alkoxy, nitro, amino, cyano, and methylthio;
R represents a member selected from the group consisting of COOH, COO-(lower alkyl), $CONH_2$, CONH-(lower alkyl) and CON-(lower alkyl)$_2$;
$R_1$ represents lower alkyl;
$R_2$ represents a member selected from the group consisting of hydrogen and lower alkyl, provided that when said $Ar_1$ is a member of the group consisting of nitrosubstituted phenyl, then, with regard to Formula III, $R_2$ is hydrogen;
Me is methyl;
and the non-toxic, therapeutically acceptable salts of such acids, such as are obtained from the appropriate organic and inorganic bases. According to Carson, supra, the 4-substituted 5-aroylpyrrole alkanoic acids must be obtained by condensation of the appropriate 1-aryl-1,2,3-butanetrione-2-oxime and an appropriate dialkyl acetonedicarboxylate as starting materials to provide the corresponding ring closed pyrrole, alkyl 5-aroyl-3-alkoxycarbonyl-4-methylpyrrole-2-acetate; or by condensation of an appropriate chloromethyl loweralkyl ketone added to a mixture of an appropriate diloweralkyl acetonedicarboxylate, preferably the diethyl ester and a loweralkyl amine to provide the ring-closed pyrrole, alkyl 1,4-diloweralkyl-3-alkoxy-carbonyl pyrrole-2-acetate. These pyrrole intermediates are then treated as disclosed in U.S. Pat. Nos. 3,752,826 and 3,865,840 to obtain the desired 5-aroyl-4-lower alkyl-pyrrole-2-alkanoic acids and acid derivatives thereof useful as anti-inflammatory agents.

The condensation of chloromethylketone, ammonia and hydroxy crotonic acid alkylester through an anti-crotonic acid ester is taught by Fischer and Orth, *Die Chemie Des Pyrroles*, pp. 5–6 and 233–234, Edward Brothers, Inc., Ann Arbor, Mich., 1943. However, neither the 4-alkyl-substituent nor the diester functionality are disclosed in this reference.

Another pyrrole ring-closure synthesis, known as the Hantzsch pyrrole synthesis, teaches the interaction of alphachloro-aldehydes or ketones with beta-ketoesters and ammonia or amines to give pyrroles, Gowan and Wheeler, *Name Index of Organic Reactions*, p. 116, Longmans, Green and Co., Ltd. New York, N.Y., 1960.

In a similar manner, there is taught the reaction of chloroacetone with a salt produced from reaction of methyl amine and diethyl acetone dicarboxylate to give a 4-methylpyrrole, Jones and Bean, *The Chemistry of Pyrroles*, p. 59, 104, Academic Press Inc., New York, 1977. Also, the pyrrole synthesis from chloromethyl ketones and beta-ketocarboxylic esters with ammonia or amines is known, Krauch and Kunz, *Organic Name Reactions*, p. 211, John Wiley and Sons, Inc., New York, 1964. However, such teachings either fail to suggest the possibility of the pyrrole diester compounds or teach no more than Carson, supra, and are based thereon.

Specifically pertinent to the improved process of this invention, U.S. Pat. Nos. 3,752,826 and 3,865,840 teach that after reaction of, for example, aqueous methyl-amine with diethyl acetone-dicarboxylate and then adding chloroacetone at a temperature below 60° C. for a period of two hours, the resultant reaction mixture is poured into ice-hydrochloric acid. The acidification acts to dehydrate the intermediate dihydroxy pyrrolidine to the desired pyrrole. However, it was discovered that prior to acidification the intermediate reaction mixture contained only minimal amounts of the desired 1,4-diloweralkyl-3-loweralkoxycarbonyl-pyrrole-2-acetic acid ester when analyzed by NMR. In contrast, upon analysis by vapor phase chromatograph of an aliquot of the same sample, a major amount of the desired ester was shown. This indicated heating in the chromatograph injection port at about 100° C. was responsible.

THE INVENTION

Based on the discovery that increased amounts of the desired ester are produced from contact of the intermediate reaction mixture with high temperatures, the present invention provides an improved process for the preparation of a loweralkyl 1,4-diloweralkyl-3-loweralkoxycarbonyl-pyrrole-2-acetate of the formula:

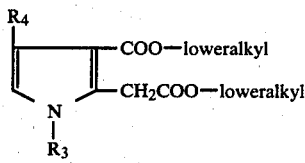

by reacting a mixture of a chloromethyl loweralkyl ketone of the formula: Cl—$CH_2$—CO—$R_4$, with a diloweralkyl acetone dicarboxylate of the formula:

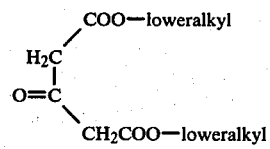

and a loweralkylamine of the formula: $R_3$—$NH_2$, wherein the foregoing formulas said $R_3$ and said $R_4$ represent loweralkyl, the improvement comprising said reacting being carried out in a two-stage procedure according to the steps of (a) adding said chloromethylloweralkyl ketone to a pre-mixed cooled solution of said loweralkylamine and said dicarboxylate in a suitable solvent with reaction at below 60° C., and (b) heating the resulant reaction mixture to from about 70° to about 100° C. for a period sufficient to dehydrate the dihydroxy pyrrolidine intermediate in said resultant reaction mixture and produce the desired loweralkyl 1,4-diloweralkyl-3-loweralkoxycarbonyl-pyrrole-2-acetate.

As used in this invention, "loweralkyl" and "loweralkoxy" may be straight or branch chained saturated hydrocarbons having from 1 to 6 carbon atoms, such as, for example, methyl, ethyl, propyl, isobutyl, isopropyl, butyl, pentyl, hexyl and the like alkyls and, respectively, the corresponding alkoxys such as methoxy, ethoxy, propoxy, isopropoxy, etc.

The loweralkyl 1,4-diloweralkyl-3-loweralkoxycarbonylpyrrole-2-acetate of the present invention is preferably produced when the chloromethyl loweralkyl ketone is a chloroacetone. Chloroacetone is a readily available and relatively inexpensive ketone. The dicarboxylate is preferably dimethyl or diethyl acetone dicarboxylate which can be prepared according to known procedures. The other reactant is a loweralkylamine, preferably methylamine in order to have a 1-methylpyrrole compound produced. Should other 1-substituted pyrroles be desired, then other amines such as aryl amines or other alkyl amines, are also suitable reactants in the process of this invention. However, preferably, in order to produce the 1,4-diloweralkyl pyrrole compound, methylamine is used. Preferably, a 40% solution of methylamine is employed since this is conveniently available. More preferably, the solution is a 40% aqueous solution of methylamine.

The reaction of, for example, diethyl acetone dicarboxylate, methylamine and chloroacetone is carried out by adding the diethyl acetone dicarboxylate to a cooled mixture of aqueous methylamine and then adding portionwise chloroacetone while maintaining a temperature below about 60° C. In this respect, Step (a) of the invention as given in the procedure above is conventional and known in the Carson references, supra. However, instead of pouring the resultant mixture into ice and hydrochloric acid, the reaction mixture is heated to distill any solvent and methylamine from the reaction mixture leaving the desired product. It appears that to have adequate temperatures, the heating should be carried out at greater than 70° C. and preferably between 80° and 100° C. Preferably, after adequate time for reaction of the methylamine, diethyl acetone carboxylate and chloroacetone, it is only necessary to heat the reaction mixture to temperature after which it is cooled and the solids separated from the reaction resultant solution, if desired.

Preferably, the entire reaction sequence can be carried out in a suitable solvent. Solvents suitable for both steps of the reaction have been found to be those which have boiling points at atmospheric pressure greater than about 100° C., which maintain the reactants in solution and which can be easily distilled from the desired pyrrole diester product. It has been found that chlorinated hydrocarbon solvents such as chloroform can be employed. Further, methylene chloride is also a suitable reaction solvent. Aromatic hydrocarbons such as toluene also are useful reaction solvents. Further, because the methylamine comes as an aqueous solution, it has been found that water itself can be an adequate solvent. Finally, aqueous mixtures of hydrocarbons and chlorinated hydrocarbons from the use of methylene chloride, chloroform or toluene with aqueous methylamine can also be used as solvents.

Following heating to the desired temperature, the dehydrated product can be separated from the reaction mixture by extraction such as with methylene chloride or other suitable solvent. Alternatively, the solvent can be distilled off and leave the desired product. In a preferred procedure, diethyl acetone dicarboxylate was added to a solution of methylamine in chloroform over a period of one minute to give a white gel-like solid. Then, while cooling, chloroacetone was added portionwise at 20° C. The reaction mixture temperature rose to 25°, then cooling was removed and the reaction mixture was stirred at room temperature. After 35 minutes, an aliquot was removed and analyzed by NMR. The NMR analysis showed a complicated mixture with very little, if any, of the pyrrole diester present. The aliquot was then heated to distill off the chloroform and then redissolved in deuterated chloroform. At this point, analysis by NMR showed the pyrrole diester was present. Subsequent vapor phase chromatographic analysis in equipment employing a 10% SE—52 column from 100° C. at 10° per minute showed 81 area percent of the desired pyrrole diester.

The thermal dehydration technique has numerous advantages. One of them is the saving of about 8 equivalents of hydrochloric acid required to acidify the large amounts of methylamine. A further subsequent saving of 8 equivalents of caustic required to regenerate the methylamine from its hydrochloride salt for recycle is concurrently realized. Advantageously, the yields for the prior art acidic dehydration and the thermal dehydration reactions are about the same within experimental error. Still further, the thermal dehydration technique allows the subsequent steps such as conversion of the ester to the diacid to be carried out in the same added slowly to the mixture. The product was extracted with methylene chloride and the solvent evaporated to produce a tan to white solid product.

TABLE I

Preparation of Ethyl 1,4-dimethyl-3-ethoxycarbonylpyrrole-2-acetate (PDE) by Reaction of Methylamine (MA), Diethyl Acetone Dicarboxylate (ADC) and Chloroacetone (CA) Optionally Followed by Saponification to the Diacid (PDA)

| Example No. | Mole Ratio CA/ADC | Mole Ratio MA/ACC | Solvent | Dehydration Technique* | Yield PDE | Yield PEA* | Yield PDA |
|---|---|---|---|---|---|---|---|
| 2 | 2 | 8.2 | CHCl$_3$ | 61° C. | 52 | 5 | — |
| 3 | 2 | 9.0 | φCH$_3$H$_2$O | 80° C. | 55 | 2 | — |
| 4 | 2 | 8.0 | CHCl$_3$ | 61° C. | — | — | 55 |
| 5 | 1.25 | 5.0 | CH$_2$Cl$_2$/H$_2$O | 90° C. | 61 | 2 | — |
| 6 | 1.25 | 7.2 | CH$_2$Cl$_2$/H$_2$O | 90° C. | — | — | 64 |
| 7 | 1.25 | 7.2 | CH$_2$Cl$_2$/H$_2$O | 90° C. | 63 | 2 | — |
| Comparative Examples | | | | | | | |
| 8 | 2 | 8.2 | CHCl$_3$ | 22°–50° C. | 65 | 3 | — |
| 9 | 2 | 9.0 | H$_2$O | 22°–42° C. | 48 | 3 | — |
| 10 | 2 | 9.0 | φCH$_3$/H$_2$O | 15°–44° C. | 57 | 2 | — |
| 11 | 1.35 | 8.2 | CH$_2$Cl$_2$/H$_2$O | 25°–36° C. | — | — | 67 |
| 12 | 1.4 | 8.5 | CH$_2$Cl$_2$/H$_2$O | 25° C. | — | — | 65 |

*1,4-dimethyl-3-ethoxycarbonyl-pyrrole-N-methyl acetamide.

equipment since a filtration or centrifugation step of the resultant ester is eliminated because the acidification is no longer required. Thus, the ester can be directly treated with water and caustic in the same reactor to saponify the ester to the acid.

The following examples are illustrative of the thermal dehydration technique of the present invention.

EXAMPLE 1

In a suitable reaction vessel, to 25 ml of a 40% solution of aqueous methylamine (291 mmoles), cooled by an ice water bath, was added 6.68 grams of diethyl acetone dicarboxylate (32.4 mmoles) in one-half minute. Then chloroacetone was added to the resultant mixture over about 2 minutes and the temperature reached about 42° C. After stirring vigorously for one hour at room temperature, the reaction mixture was heated with an oil bath to a temperature of 92° C. over a period of 20 minutes.

After cooling, the product was extracted with chloroform and the solvent evaporated to give 10 grams of a reddish oil. Analysis by NMR indicates the product contains primarily ethyl 1,4-dimethyl-3-ethoxycarbonyl-pyrrole-2-acetate and chloroform. Yield of product was 50% with an additional 2% of 1,4-dimethyl-3-ethoxycarbonyl-pyrrole-N-methyl acetamide.

In a similar manner, several other thermal dehydration examples of the present invention were carried out together with comparative acid dehydrations as known in the prior art. The results of such experiments using varying conditions of reactant ratios and solvents are given in the following table in which Examples 2–7 are examples of this invention and comparative runs 8–12 use acidification with hydrochloric acid to dehydrate the intermediate to the desired ethyl 1,4-dimethyl-3-ethoxycarbonyl-pyrrole-2-acetate.

The general procedure followed for the acid dehydrations was to add, to a suitable reaction vessel, a 40% solution of aqueous methylamine to a solution of diethyl acetone dicarboxylate and chloroacetone in methylene chloride. A dry-ice/acetone condenser was used to condense methylamine and methylene chloride. Initial reaction temperature was approximately 25° C. which generally increased to approximately 38° C. (reflux) within five minutes. After stirring the reaction mixture for about 0.5 hour, concentrated hydrochloric acid was It should be recognized that similar results are obtainable from thermal dehydration of other loweralkyl ester groups where R$_3$ and R$_4$ are methyl, propyl, isopropyl, pentyl and hexyl.

The Carson patents, U.S. Pat. Nos. 3,752,826 and 3,865,840, are hereby incorporated by reference as if fully set forth.

Having disclosed the process of the present invention, one skilled in the art can readily envision variations, modifications and changes within the scope and spirit of this invention. Therefore, it is desired that the present invention be limited only by the lawful scope of the following claims.

What is claimed is:

1. In a process for the preparation of a loweralkyl 1,4-diloweralkyl-3-loweralkoxycarbonyl-pyrrole-2-acetate of the formula:

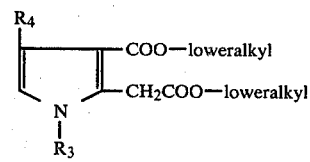

by reacting a mixture of a chloromethyl loweralkyl ketone of the formula: Cl—CH$_2$—CO—R$_4$, with a diloweralkyl acetone dicarboxylate of the formula:

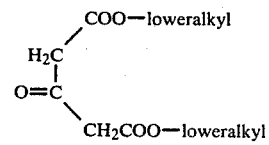

and a loweralkylamine of the formula: R$_3$NH$_2$, wherein the foregoing formulas said R$_3$ and said R$_4$ represent loweralkyl, the improvement consisting essentially of said reaction being carried out in a two-stage procedure according to the steps of (a) adding said chloromethylloweralkyl ketone to a pre-mixed cooled solution of said loweralkylamine and said dicarboxylate in a suitable solvent with reaction at below 60° C., and (b) heating the resultant reaction mixture to from about 70° to about 100° C. for a period sufficient to dehydrate the dihydroxy pyrrolidine intermediate in said resultant reaction mixture and produce the desired loweralkyl 1,4-diloweralkyl-3-loweralkoxycarbonyl-pyrrole-2-acetate.

2. The improved process of claim 1 wherein said dicarboxylate is diethyl acetone dicarboxylate.

3. The improved process of claim 1 wherein said dicarboxylate is diethyl acetone dicarboxylate and said loweralkylamine is methylamine.

4. The improved process of claim 1 wherein said dicarboxylate is diethyl acetone dicarboxylate, said loweramine is methylamine and said ketone is chloroacetone.

5. The improved process of claim 1 wherein said solvent is chloroform.

6. The improved process of claim 1 wherein said solvent is water.

7. The improved process of claim 1 wherein said solvent is toluene.

8. The improved process of claim 1 wherein said solvent is selected from the group consisting of chloroform, toluene, water and aqueous mixtures of toluene and chloroform.

9. The improved process of claim 1 wherein said Step (b) the heating is carried out at a temperature greater than 90° C.

10. The improved process of claim 1 wherein the heating of said Step (b) is carried out at a temperature from 80° to about 100° C.

11. The improved process of claim 1 wherein the loweralkyl 1,4-diloweralkyl-3-loweralkoxycarbonyl-pyrrole-2-acetate produced is further reacted by contacting with a suitable alkali metal hydroxide for a suitable period to convert the ester groups to acid producing a 1,4-diloweralkyl-3-hydroxycarbonyl-pyrrole-2-acetic acid.

* * * * *